United States Patent [19]

Beppu et al.

[11] Patent Number: 4,703,128
[45] Date of Patent: Oct. 27, 1987

[54] GUANIDYLFUNGIN DERIVATIVES AND THEIR PRODUCTION

[75] Inventors: Teruhiko Beppu, Tokyo; Kazutoh Takesako; Teruya Nakamura, both of Kusatsu; Akira Obayashi, Uji, all of Japan

[73] Assignee: Takahara Shuzo Co., Ltd., Kyoto, Japan

[21] Appl. No.: 885,818

[22] Filed: Jul. 18, 1986

Related U.S. Application Data

[62] Division of Ser. No. 787,320, Oct. 15, 1985, abandoned.

[30] Foreign Application Priority Data

Oct. 15, 1984 [JP] Japan .................................. 59-214289

[51] Int. Cl.[4] .................. C07D 315/00; C07D 325/00
[52] U.S. Cl. .................................... 549/270; 549/269; 549/266
[58] Field of Search ............... 549/264, 265, 267, 269, 549/270, 271, 272

[56] References Cited

U.S. PATENT DOCUMENTS 4,229,466  10/1980  Mujazaki et al. .................... 549/264

OTHER PUBLICATIONS

Samain et al., J. Am. Chem. Soc., 104, pp. 4129–4141, (1982), Structure of Scopafunjin.
Gaylord, Reduction with Complex Metal Hydrides, pp. 711–719, (1956), Interscience Publications, N.Y.
Arai et al. II, CA 100:190301c, Isolation of Neocapiamycin A from Streptomycis, (1984), J. Anti 37(2), pp. 103–109.
Arai et al. I, CA 98:197839h, Studies on Macrocyclic Lactone Antibiotics VI, 1983.

Keller–Schierlein et al., CA 99:53438, Metabolic Products of Microorganisms Part 219, 1983.
Chem. Pharm. Bull., vol. 30, p. 1669, (1982).
Chem. Pharm. Bull., vol. 30, p. 4006, (1982).
Journal of Antibiotics, vol. 35, p. 1480, (1980).
Journal of Antibiotics, vol. 37, p. 103, (1984).

*Primary Examiner*—Glennon H. Hollrah
*Assistant Examiner*—D. Dinner
*Attorney, Agent, or Firm*—Wenderoth, Lind & Ponack

[57] ABSTRACT

The feature of the present invention is a process for preparing compounds represented by general formula (Ia) described below:

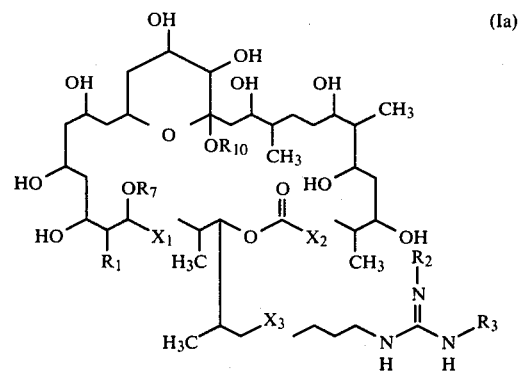

wherein $X_1$, $X_2$, $X_3$, $R_1$, $R_2$, $R_3$ and $R_7$ are as defined in formula (I) and $R_{10}$ represents a lower alkyl group, or acid salts thereof, which process is characterized by using the guanidylfungins (II) as raw materials, reacting these guanidylfungins with alcohols (III) in the presence of an acid catalyst, and then hydrolyzing the malonic acid monoester (IV).

2 Claims, No Drawings

GUANIDYLFUNGIN DERIVATIVES AND THEIR PRODUCTION

This application is a division of now abandoned application Ser. No. 787,370, filed Oct. 15, 1985.

The present invention relates to guanidylfungin derivatives, which are novel compounds useful as an antimicrobial substance, and a process for producing them.

PRIOR ART

Guanidylfungin A (same as 662-A) is a compound from a culture broth of a microorganism beglonging to the genus Streptomyces that is capable of producing guanidylfungin A isolated by the present inventors (Japanese Patent Application KOKAI No. 170482/83), which has the following structure.

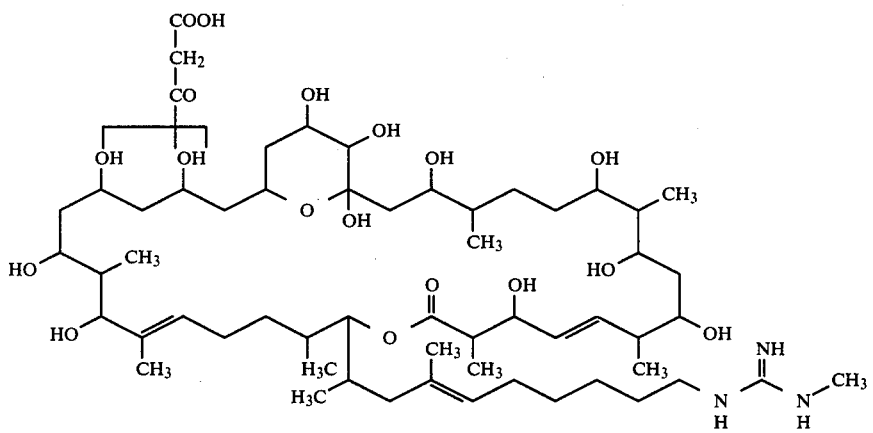

As compounds analogous to guanidylfungin A, there are methylguanidylfungin A (same as 662-A', Japanese Patent Application KOKAI No. 170482/83), guanidylfungin B (Japanese Patent Application Ser. No. 130020/84), azalomycin $F_4$ [Chem. Pharm. Bull, vol. 30, page 1669 (1982)], azalomycins $F_3$ and $F_4$ [Chem. Pharm. Bull., vol. 30, page 4006 (1982)], scopafungin [J. Am. Chem. Soc., vol. 104, page 4129 (1982)], copiamycin [Journal of Antibiotics, vol. 35, page 1480 (1980)], niphimycin [Helv. Chim. Acta, vol. 66, page 226 (1983)], and neocopiamycin A [Journal of Antibiotics, vol. 37, page 103 (1984)]. With respect to scopafungin, it has been recently found that the chemical structure published in the above-described publication was incorrect and that scopafungin has the same structure as that of niphimycin [Helv. Chim. Acta, vol. 67, page 696 (1984)]. These compounds are characterized by all containing a guanidyl group, a 6-membered hemiketal ring, a lactone ring, and a malonic acid monoester in their structures. In addition, their antimicrobial spectra are similar to one another and these compounds all have antimicrobial activity against Gram-positive bacteria and fungi.

In the present invention, compounds having the above-mentioned structural characteristics are collectively referred to as the guanidylfungins.

Among the guanidylfungins, azalomycin F has been used clinically for treatment of vaginal trichomonoiasis. When compared with amphotericin B, widely used as an antimycotic, the antimicrobial activity of conventional guanidylfungins is weak, fungistatic, and insufficient as antimycotics. Further, the known antibiotics of the guanidylfungins are disadvantageous in that they have a low solubility in water and alcohol.

Recently, it has been noted that with regard to copiamycin and azalomycin F among the guanidylfungins, the antimicrobial activity is potentiated by use in combination with the imidazole antimycotics such as ketoconazole, clotrimazole, miconazole, etc. (Japenese Patent Application KOKKAI No. 67221/84). The imidazole antimycotics have strong antimicrobial activity both in vitro and in vivo and have thus been expected to be useful in treating fungal infections against which a few chemotherapeutic agents are effective, but the toxicity of these antimycotics is not always low. Further investigation is needed of clinical use of such antimycotics. However, by the use of copiamycin in combination with such antimycotics, it has become possible to overcome somewhat the disadvantage, and attention has been focused thereon. Among the imidazole antimycotics, clotrimazole and miconazole are commercially available in Japan as medicines for external application.

PROBLEM TO BE SOLVED BY THE INVENTION

As described above, the guanidylfungins are useful as antimycotics but the known antibiotics of the guanidylfungins are unsatisfactory in their antimicrobial activity and solubility.

An object of the present invention is to provide novel demalonyl derivatives of the guanidylfungins which eliminate the above-described problems, and also processes for preparing such derivatives.

MEANS FOR SOLVING THE PROBLEM

Briefly, the first feature of the present invention is to provide compounds represented by general formula (I) described below:

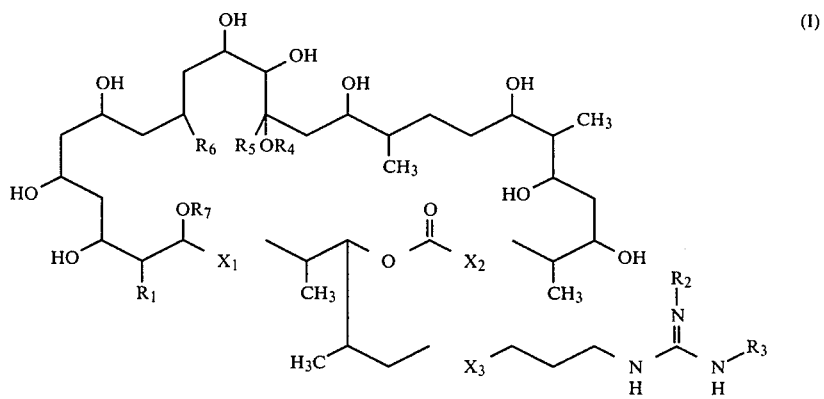
(I)

wherein
X₁ represents

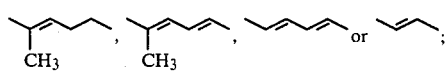

X₂ represents

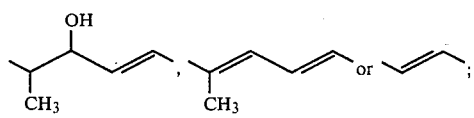

X₃ represents

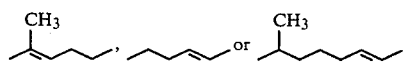

$R_1$ represents H or $CH_3$;
$R_2$ and $R_3$ which may be the same or different, each represent H or a lower alkyl group;
for $R_4$, $R_5$ and $R_6$, $R_4$ is a lower alkyl group, $R_5$ and $R_6$ are one ether bond, or else $R_4$ is H, $R_5$ is H, and $R_6$ is OH;
$R_7$ represents H or a lower alkyl group; or acid salts thereof.

Next, the process for preparing the compounds of general formula (I) of the present invention will be explained with reference to the second and third features of the present invention.

The second feature of the present invention is a process for preparing compounds represented by general formula (Ia) described below:

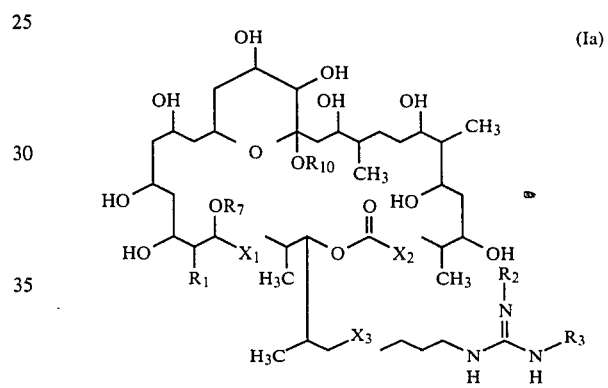

wherein $X_1$, $X_2$, $X_3$, $R_1$, $R_2$, $R_3$ and $R_7$ are as defined in formula (I) and $R_{10}$ represents a lower alkyl group, or acid salts thereof, which process is characterized by using the guanidylfungins (II) as raw materials, reacting these guanidylfungins with alcohols (III) in the presence of an acid catalyst, and then hydrolyzing the malonic acid monoester (IV), as shown in the following scheme:

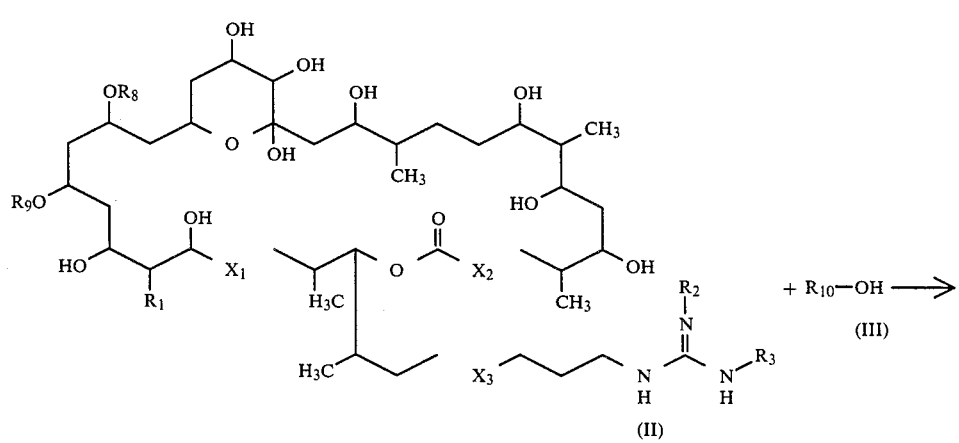

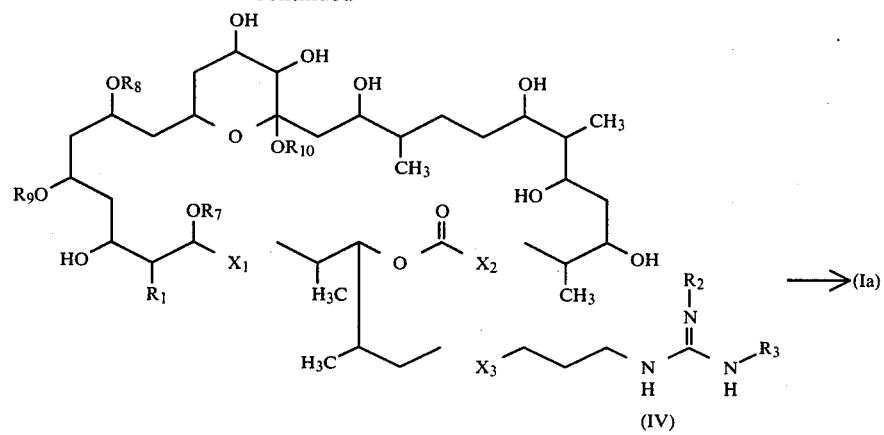

(IV)

The third feature of the present invention is a process for preparing compounds represented by general formula (Ib) described below:

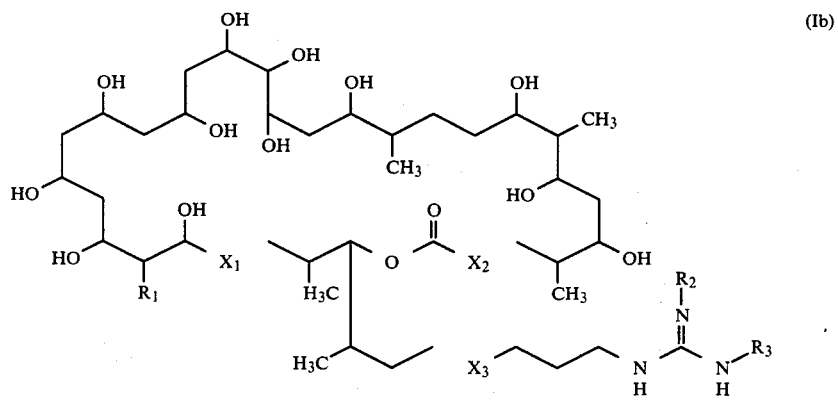

(Ib)

wherein $X_1$, $X_2$, $X_3$, $R_1$, $R_2$ and $R_3$ are as defined in formula (I), or acid salts thereof, which process is characterized by using the guanifylfungins (II) as raw materials, reacting them with reducing agents to reduce the hemiketal group to compounds (V), and then hydrolyzing the malonic acid monoester, as shown in the following scheme:

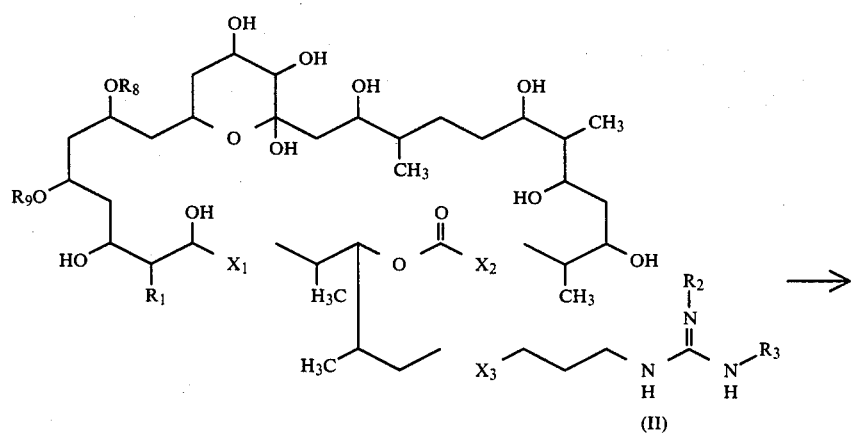

(II)

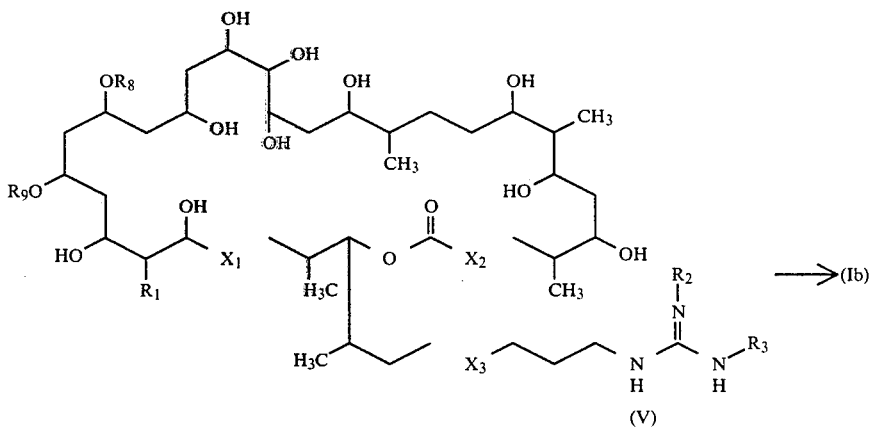

As described above, the present inventors have found that by removing the malonic acid monoester present in the guanidylfungins, antimicrobial activity is enhanced and at the same time, solubility in water and alcohols is increased.

Hereafter the present invention will be described in detail.

The gist of the first feature of the present invention resides in the compounds represented by general formula (I) or its acid salts thereof.

Typical examples of the compounds represented by general formula (I) are shown in Table 1 and physicochemical properties of the hydrochlorides thereof are shown in Table 2.

The hydrochlorides of these compounds have greater solubility in water and alcohols compared to the raw materials. For example, the hydrochloride of Compound 11 has a solubility of about 15 mg/ml in water and 40 mg/ml in ethanol but copiamycin, the raw material of 11 is sparingly soluble in water (less than 1 mg/ml), and soluble only about 20 mg/ml in ethanol.

The compounds of general formula (I) form salts with acids. As the acids used for forming the salts, any inorganic acid or organic acid may be used, with no particular limitation.

The antimicrobial activity of each of the compounds shown in Table 1 and the corresponding raw materials (cf. Table 4) was examined by measuring the minimal inhibitory concentration (MIC) and the minimal fungicidal concentration (MCC) by a dilution method in liquid medium.

That is, $2 \times 10^6$ cells/ml of *Candida albicans* or $5 \times 10^5$ spores/ml of *Asperillus fumigatus* IAM 2046 were inoculated on Sabraud dextrose agar medium containing a known concentration of a compound followed by culturing at 30° C. for 24 hours. The concentration of the compound at which no turbidity due to the growth of bacteria was observed by the naked eye was designated as the MIC.

Further, 0.1-ml portions of a culture fluid of each compound cultured in a concentration as described above were taken and each was spread over fresh Sabraud dextrose agar and cultured again at 30° C. After cultivation for 48 hours, the concentration of the compound at which over 10 colonies did not form was designated as the MCC.

The MIC for *Staphylococcus aureus* 209P was determined using heart infusion broth in the same way as finding MIC described above except that the culture temperature was at 37° C.

The test results are shown in Table 3.

As is evident from Table 3, increased antimicrobial activity was noted with Compounds 1, 3, 5, 7, 9, 11, 13 and 15 as compared to the raw materials. In particular, the increase was remarkable with Compounds 1, 3, 11 and 13. Further in the case of Compounds 5, 7, 9 and 15, the enhancement of MCC was remarkable.

Further in the case of Compounds 2, 4, 6, 8, 10, 12 and 14, enhancement of antimicrobial activity was obviously noted in the MCC.

TABLE 1

(I)

[Structure of compound (I) with substituents $R_1$–$R_7$ and $X_1$, $X_2$, $X_3$]

| Compound | $X_1$ | $X_2$ | $X_3$ | $R_1$ | $R_2$ | $R_3$ | $R_4$ | $R_5$ | $R_6$ | $R_7$ |
|---|---|---|---|---|---|---|---|---|---|---|
| 1 | $-CH_2CH_2CH=C(CH_3)CH_3$ | $-CH(CH_3)CH(OH)CH=CH-$ | $-CH_2CH_2CH=C(CH_3)CH_3$ | $CH_3$ | H | $CH_3$ | $CH_3$ | O (ether bond) | | H |
| 2 | " | " | " | " | " | " | H | H | OH | " |
| 3 | " | " | " | " | " | H | $CH_3$ | O (ether bond) | | " |
| 4 | " | " | " | " | " | " | H | H | OH | " |
| 5 | $-CH=CH-CH=C(CH_3)CH_3$ | $-CH=CH-CH=C(CH_3)CH_3$ | $-CH_2-CH=CH-CH_2-$ | H | H | $CH_3$ | $CH_3$ | O (ether bond) | | $CH_3$ |
| 6 | " | " | " | " | " | " | H | H | OH | H |
| 7 | " | " | " | " | H | H | $CH_3$ | O (ether bond) | | $CH_3$ |
| 8 | " | " | " | " | " | " | H | H | OH | H |
| 9 | " | " | " | " | $CH_3$ | $CH_3$ | $CH_3$ | O (ether bond) | | $CH_3$ |
| 10 | " | " | " | " | " | " | H | H | OH | H |
| 11 | $-CH=CH-$ | $-CH=CH-$ | $-CH(CH_3)CH_2CH_2CH_2CH=CH-$ | $CH_3$ | H | $CH_3$ | $CH_3$ | O (ether bond) | | H |
| 12 | " | " | " | " | " | " | H | H | OH | " |
| 13 | " | " | " | " | " | H | $CH_3$ | O (ether bond) | | " |
| 14 | " | " | " | " | " | " | H | H | OH | " |
| 15 | $-CH=CH-CH=CH-$ | $-CH(CH_3)CH(OH)CH=CH-$ | $-CH(CH_3)CH_2CH_2CH_2CH=CH-$ | $CH_3$ | H | $CH_3$ | $CH_3$ | O (ether bond) | | H |
| 16 | " | " | " | " | " | " | H | H | OH | " |

TABLE 2

| Compound | Melting Point (°C.) | SIMS*1 (m/z; M + H) | Molecular Formula | IR (KBr)(cm⁻¹) | UV (Methanol) [λ$_{max}$nm(ε)] | ¹³σ NMR(σD₃OD, 25 MHz)*² [δ$_{ppm}$ (TMS as standard)] |
|---|---|---|---|---|---|---|
| 1 | 122–125 | 1058 | C₅₆H₁₀₃N₃O₁₅·HCl | 3400, 2980, 2940, 1710, 1640, 1460, 1380, 1260, 1130, 1090, 1040, 1000, 980 | end absorption | 176.7, 158.1, 137.4, 136.7, 134.0, 132.3, 128.8, 127.9, 102.4 81.3, 81.1, 76.6, 76.2, 75.0, 72.3, 71.8, 69.3, 66.4, 66.1, 45.5, 45.0, 43.4, 43.0, 42.5, 41.8, 40.6, 39.0, 35.7, 35.1, 33.2, 30.4, 29.8, 28.7, 28.3, 27.3, 25.3, 17.0, 16.0, 15.1, 14.5, 13.4, 11.8, 11.2, 10.5 |
| 2 | 110–116 | 1046 | C₅₅H₁₀₃N₃O₁₅·HCl | 3400, 2980, 2940, 1710, 1640, 1560, 1450, 1400, 1380, 1260, 1180, 1060, 970 | | 177.0, 158.4, 137.5, 136.5, 134.2, 132.5, 128.4, 128.0, 81.5, 77.5, 76.0, 75.2, 73.1, 72.3, 69.6, 66.6, 45.9, 45.4, 44.2, 43.5, 42.5, 41.6, 39.4, 35.4, 33.1, 30.4, 29.8, 29.2, 28.7, 28.4, 27.2, 22.5, 17.2, 16.2, 16.1, 15.6, 15.1, 13.6, 11.8, 11.4, 10.6, 25.5, 17.2, 16.2, 16.1, 15.6, 15.1, 13.6, 11.8, 11.4, 10.6 |
| 3 | 118–121 | 1044 | C₅₅H₁₀₁N₃O₁₅·HCl | 3400, 2980, 2940, 1710, 1640, 1460, 1380, 1260, 1100, 1050, 980 | | |
| 4 | 108–112 | 1032 | C₅₄H₁₀₁N₃O₁₅·HCl | 3400, 2980, 2940, 1700, 1650, 1460, 1380, 1260, 1050, 980 | | |
| 5 | 121–126 | 1024 | C₅₅H₉₇N₃O₁₄·HCl | 3370, 2970, 2950, 1680, 1650, 1460, 1390, 1250, 1100, 980 | 268 (21000) 240 (35000) | 169.7, 158.0, 145.9, 140.2, 139.9, 136.9, 136.0, 132.4, 129.9, 127.8, 124.4, 126.6, 102.3, 84.5, 80.4, 76.4, 75.3, 72.3, 71.9, 62.2, 66.3, 65.7, 56.6, 47.7, 45.0, 44.7, 44.0, 41.7, 41.0, 40.8, 35.0, 34.7, 33.5, 33.0, 30.3, 29.6, 28.2, 27.8, 17.0, 13.9, 12.6, 12.0, 10.4 |
| 6 | 103–107 | 998 | C₅₃H₉₅N₃O₁₄·HCl | 3350, 2970, 2950, 1680, 1650, 1460, 1380, 1260, 1100, 1030, 970, | 267 (22000) 240 (37000) | 169.9, 158.1, 145.8, 140.0, 135.9, 132.4, 130.0, 128.3, 127.5, 126.6, 125.0, 81.0, 77.3, 75.6, 75.1, 74.1, 73.2, 72.3, 69.2, 66.5, 46.0, 44.6, 44.0, 41.9, 40.7, 39.7, 39.3, 35.4, 34.2, 33.6, 33.4, 30.4, 29.7, 29.2, 28.3, 27.8, 18.0, 17.4, 15.5, 14.5, 13.3, 12.9, 10.5, |
| 7 | 118–122 | 1010 | C₅₄H₉₅N₃O₁₄·HCl | 3400, 2970, 2950, 1640, 1450, 1380, 1250, 1100, 980 | 268 (21000) 240 (35000) | |
| 8 | 105–109 | 984 | C₅₂H₉₃N₃O₁₄·HCl | 3400, 2970, 2950, 1680, 1640, 1450, 1380, 1250, 1050, 980 | 268 (21000) 240 (35000) | |
| 9 | 115–119 | 1038 | C₅₆H₉₉N₃O₁₄·HCl | 3400, 2970, 2950, 1680, 1640, 1450, 1370, 1250, 1100, 980 | 268 (22000) 240 (37000) | |
| 10 | 199–103 | 1012 | C₅₄H₉₇N₃O₁₄·HCl | 3400, 2970, 2950, 1670, 1640, 1450, 1370, 1250, 1100, 1040, 980 | 268 (22000) 240 (37000) | |
| 11 | 131–136 | 986 | C₅₂H₉₅N₃O₁₄·HCl | 3400, 2970, 2940, 1700, 1680, 1650, 1465, 1380, 1250, 1150, 1100, 980 | 205 (19000) | 168.3, 158.1, 152.9, 136.3, 135.6, 132.7, 130.0, 123.6, 102.5, 79.3, 76.6, 75.4, 74.8, 72.3, 71.7, 69.4, 66.9, 65.9, 65.2, 45.8, 44.6, 42.6, 41.9, 41.3, 40.3, 37.7, 33.7, 31.9, 30.6, 30.4, 29.8, 28.3, 27.8, 20.4, 17.1, 16.3, 14.4, 13.5, 10.4, 9.8 |
| 12 | 98–101 | 974 | C₅₁H₉₅N₃O₁₄·HCl | 3350, 2970, 2940, 1650, 1465, 1385, 1160, 1020, 980, | 205 (19000) | 168.1, 157.9, 152.6, 134.6, 134.0, 132.6, 129.8, 122.8, 80.0, 77.3, 75.7, 75.5, 75.0, 73.0, 72.0, 69.4, 66.5, 46.0, 44.9, 44.3, 43.9, 42.5, 41.9, 40.1, 39.8, 37.4, 33.7, 32.5, 30.5, 29.6, 29.2, 28.3, 27.7, 20.4, 17.8, 15.4, 14.7, 11.5, 10.5, |

TABLE 2-continued

| Compound | Melting Point (°C.) | SIMS[*1] (m/z; M + H) | Molecular Formula | IR (KBr)(cm$^{-1}$) | UV (Methanol) [λ$_{max}$,nm(ε)] | $^{13}$σ NMR(σD$_3$OD, 25 MHz)[*2] [δ$_{ppm}$ (TMS as standard)] |
|---|---|---|---|---|---|---|
| 13 | 129–134 | 972 | C$_{51}$H$_{93}$N$_3$O$_{14}$·HCl | 3350, 2980, 2950, 1670, 1465, 1380, 980 | 205 (18000) | |
| 14 | 95–99 | 960 | C$_{50}$H$_{93}$N$_3$O$_{14}$·HCl | 3350, 2980, 2950, 1650, 1460, 1380, 1160, 1040, 980 | 205 (18000) | |
| 15 | 123–126 | 1070 | C$_{57}$H$_{103}$N$_3$O$_{15}$·HCl | 3400, 2980, 2950, 1720, 1650, 1460, 1390, 1260, 1140, 1100, 1070, 1000, | 231 (5000) | 176.4, 158.1, 137.0, 135.0, 132.1, 129.8, 102.5, 79.5, 76.6, 76.0, 75.2, 72.1, 69.3, 68.9, 66.2, 66.1, 45.3, 45.0, 43.5, 42.6, 41.9, 41.0, 40.8, 39.0, 37.5, 35.4, 33.8, 32.4, 30.5, 29.7, 28.3, 27.8, 20.3, 17.7, 16.9, 14.9, 14.5, 10.9, 10.3, |
| 16 | 92–97 | 1058 | C$_{56}$H$_{103}$N$_3$O$_{15}$·HCl | 3400, 2980, 2950, 1720, 1650, 1460, 1380, 1270, 1190, 1060, 990, | 231 (5000) | 176.5, 157.8, 136.6, 136.1, 134.8, 132.5, 132.0, 131.5, 129.6, 79.8, 77.0, 75.7, 75.5, 75.1, 73.2, 72.2, 69.5, 68.9, 66.4, 47.7, 45.8, 44.4, 43.9, 43.5, 42.3, 41.7, 40.4, 39.3, 37.1, 35.4, 33.6, 33.1, 32.4, 30.3, 29.6, 29.1, 28.2, 27.5, 20.4, 17.9, 16.9, 15.4, 14.7, 11.2, 10.5 |

[*1]Abbreviation for secondary ion mass spectrum
[*2]Because of measurement in CD$_3$OD, some of the peaks appearing at about 46–52 ppm could not be observed because they were hidden by the peak of CD$_3$OD.

TABLE 3

| Compound | Organisms Tested | | | | |
|---|---|---|---|---|---|
| | M I C (mcg/ml) | | | M C C (mcg/ml) | |
| | Staphylococcus aureus | Candida albicans | Aspergillus fumigatus | Candida albicans | Aspergillus fumigatus |
| Guanidylfungin A | 200 | 200 | >200 | >200 | >200 |
| 1 | 6.25 | 6.25 | 12.5 | 25 | 25 |
| 2 | 50 | 100 | 50 | >200 | 100 |
| Guanidylfungin B | 200 | 200 | >200 | >200 | >200 |
| 3 | 6.25 | 6.25 | 12.5 | 25 | 50 |
| 4 | 100 | 100 | 50 | >200 | 200 |
| Azalomycin F$_4$ | 12.5 | 12.5 | 25 | >200 | >200 |
| 5 | 12.5 | 12.5 | 12.5 | 25 | 50 |
| 6 | 25 | 50 | 100 | 200 | 200 |
| Azalomycin F$_3$ | 12.5 | 12.5 | 50 | >200 | >200 |
| 7 | 12.5 | 12.5 | 25 | 25 | 50 |
| 8 | 50 | 50 | 100 | 200 | 200 |
| Azalomycin F$_5$ | 12.5 | 12.5 | 50 | >200 | >200 |
| 9 | 12.5 | 12.5 | 25 | 25 | 50 |
| 10 | 50 | 50 | 100 | 200 | 200 |
| Copiamycin | 200 | 200 | >200 | >200 | >200 |
| 11 | 6.25 | 6.25 | 6.25 | 12.5 | 25 |
| 12 | 50 | 50 | 50 | 100 | 100 |
| Neocopiamycin A | 100 | 100 | >100 | >100 | >100 |
| 13 | 6.25 | 12.5 | 12.5 | 50 | 50 |
| 14 | 50 | 50 | 50 | 200 | 100 |
| Scopafungin | 12.5 | 12.5 | 25 | >200 | >200 |
| 15 | 6.25 | 6.25 | 6.25 | 12.5 | 12.5 |
| 16 | 12.5 | 12.5 | 25 | 200 | 25 |

In the second feature of the present invention, the acid catalyst that may be used in the alkylation is not particularly limited; hydrochloric acid, sulfuric acid, etc., can be used. While there is no particular limitation for the reaction temperature, it is preferred that the temperature be at temperatures lower than room temperature. The reaction time varies depending upon the reaction temperature and the amount and kind of reagent used; it ranges from several minutes to several hours. In the reaction, not only the hemiketal group but also the hydroxy group of the allyl alcohol type may be alkylated on some occasions.

The hydrolysis of the malonic acid monoester is carried out in the conventional manner. Hydrolysis with an alkali is particularly preferred, and is attained by maintaining pH at 10 to 12, for example, at room temperature for several minutes to several hours.

In the third feature of the present invention, the reduction of the hemiketal is carried out in the conventional manner; sodium borohydride is preferred. There is no particular limitation about the solvents that can be used, but water and lower alcohols are advantageously used.

The hydrolysis of the malonic acid monoester is carried out in the conventional manner; as described above, hydrolysis with an alkali is preferred.

The compounds used as raw materials in the present invention may be any of the guanidylfungins represented by general formula (II). Representative examples of the compounds include guanidylfungins A and B, azalomycins F$_3$, F$_4$ and F$_5$, copiamycin, neocopiamycin A and scopafungin (same as niphimycin). These compounds may further be converted into derivatives included in the guanidylfungin group by utilizing known reactions, and these derivatives can be used as raw materials. The structures of the aforesaid representatives of the guanidylfungins are shown in Table 4. Hereafter the preparation thereof will be briefly described.

Guanidylfungins A and B can be produced from a culture broth of a guanidylfungin A-producing organism belonging to the genus Streptomyces, for example, Streptomyces hygroscopicus No. 662 (deposition No. FERM BP-86 in the Fermentation Research Institute of the Agency of Industrial Science and Technology) in the conventional manner (Japanese Patent Application KOKAI No. 170482/83).

Azalomycins F$_3$, F$_4$ and F$_5$ can be produced from a culture broth of an azalomycin F-producing organism belonging to the genus Streptomyces, for example, Streptomyces hygroscopics var. azalomyceticus (ATCC 13810) in the conventional manner [Journal of Antibiotics, vol. 23, page 107 (1970)].

Copiamycin and neocopiamycin A can be produced from a culture broth of a copiamycin-producing organism belonging to the genus Streptomyces, e.g. Streptomyces hygroscopics var. crystallogenes (IFM 1236, ATCC 19040 [with respect to copiamycin, see Journal of Antibiotics, Ser. A, vol. 18, page 63 (1965) and, Journal of Antibiotics, vol. 37, page 103 (1984) with respect to neocopiamycin A].

Scopafungin can be produced from a culture broth of a scopafungin-producing organism belonging to the genus Streptomyces, e.g., Streptomyces hygroscopics var. enhygrus (NRRL 3664) in a conventional manner [Journal of Antibiotics, vol. 25, page 39 (1972)].

TABLE 4

(II) [Macrocyclic structure shown with substituents $OR_8$, $OR_9$, $X_1$, $R_1$, $X_2$, $X_3$, $R_2$, $R_3$, and guanidine group]

| Compound | X₁ | X₂ | X₃ | R₁ | R₂ | R₃ | R₈ | R₉ |
|---|---|---|---|---|---|---|---|---|
| Guanidylfungin A | –CH(CH₃)CH₂CH₂CH=C(CH₃)– side chain | –CH(CH₃)CH(OH)CH=CH– side chain | –CH=C(CH₃)CH₂CH₃ side chain | CH₃ | H | CH₃ | H | COCH₂COOH |
| Guanidylfungin B | " | " | " | " | " | H | " | |
| Azalomycin F₄ | –CH=C(CH₃)– side chain | –CH=C(CH₃)– side chain | –CH=CH– side chain | H | H | CH₃ | COCH₂COOH | H |
| Azalomycin F₃ | " | " | " | " | H | H | " | " |
| Azalomycin F₅ | " | " | " | " | CH₃ | CH₃ | " | " |
| Copiamycin | –CH=CH– | –CH=CH– | –CH(CH₃)CH₂CH₂CH=CH– | H | H | CH₃ | COCH₂COOH | H |
| Neocopiamycin A | " | " | " | " | H | H | H | COCH₂COOH |
| Scopafungin (Niphimycin) | –CH=CH–CH=CH– | –CH(CH₃)CH(OH)CH=CH– | –CH(CH₃)CH₂CH₂CH=CH– | CH₃ | H | CH₃ | COCH₂COOH | H |

EXAMPLES

Hereafter the present invention will be more concretely described with reference to examples, but is not deemed to be limited thereto.

EXAMPLE 1

Preparation of Compound 1

In 10 ml of methanol was suspended 1 g of guanidylfungin A. To the suspension was added 5 ml of 1N hydrochloric acid-methanol solution. After the mixture was stirred at room temperature for 20 minutes, the reaction mixture was applied to a PDS-silica gel column Prepak ®500/C18 (manufactured by Waters Associates), developed, and eluted with a methnaol-0.01M ammonium acetate aqueous solution (76:24, vol/vol) to obtain fractions containing methylguanidylfungin A. After the fractions were distilled under reduced pressure to remove the solvent, the residue was dissolved in 30 ml of acetone-water (7:3) while being warmed. After the solution was allowed to stand at room temperature overnight, the white precipitate formed was taken by filtration to obtain 0.55 g of methylguanidylfungin A.

Melting point: 144°–146° C. (decomposed).

Elemental analysis: as $C_{59}H_{105}N_3O_{18}$: Calcd. C61.94, H9.19, N3.67, O25.20. Found C61.43, H9.24, N3.55, O25.25.

Secondary ion mass spectrum (hereafter merely referred to as SIMS): m/z 1144 (M+H)

Infrared absorption spectrum (hereafter merely referred to as IR)

(KBr) (cm$^{-1}$) 3400, 2980, 2940, 1720, 1640, 1600, 1450, 1380, 1260, 1140, 1080, 1040, 980.

In 60 ml of methanol was dissolved 0.5 g of methylguanidylfungin A. To the solution was added 20 ml of a solution of 2N potassium hydroxide in water-methanol (2:1). After stirring the mixture at room temperature overnight, the reaction mixture was neutralized with a 2N hydrochloric acid aqueous solution to discontinue the reaction. Thereafter, the reaction mixture was concentrated to dryness under reduced pressure. The residue was suspended in 5 ml of water and the water-insoluble fraction was taken by filtration. The water-insoluble fraction was dissolved in 10 ml of acetone-water (7:3). After the solution was allowed to stand at room temperature for 2 days, the white precipitate formed was taken by filtration to obtain 170 mg of Compound 1.

EXAMPLE 2

Preparation of Compound 2

In 50 ml of methanol was suspended 0.5 g of guanidylfungin A. To the suspension was added a solution of 1 g of sodium borohydride in 10 ml of methanol. After stirring at room temperature overnight, the system was neutralized with a 1N hydrochloric acid aqueous solution to stop the reaction. The reaction mixture was concentrated to dryness under reduced pressure and water was added to the residue. The water-insoluble fraction was collected by filtration to obtain 300 mg of reduced guanidylfungin A.

Melting point: 118°–122° C.
SIMS m/z 1132 (M+H).
IR (KBr) (cm$^{-1}$) 3400, 2980, 2940, 1720, 1640, 1600, 1460, 1380, 1300, 1250, 1040, 980.

In 20 ml of methanol was dissolved 130 mg of the reduced product, and 6 ml of a 2N sodium hydroxide aqueous solution was added to the solution. After stirring at room temperature overnight, the system was neutralized with a 1N hydrochloric acid aqueous solution to stop the reaction. The reaction mixture was concentrated under reduced pressure. After removing the solvent by distillation, the residue was applied to a column packed with 300 ml of Dia Ion ®HP-20 (manufactured by Mitsubishi Chemical Industries, Ltd.). After washing with water, the column was eluted with methanol. The eluate was concentrated to dryness under reduced pressure to otain 40 mg of the desired Compound 2.

EXAMPLE 3

Preparation of Compound 3

In 5 ml of methanol was suspended 50 mg of guanidylfungin B, and 1 ml of a 2N hydrochloric acid-methanol solution was added to the suspension under ice cooling. The mixture was allowed to stand at room temperature. Thereafter OH type ion exchange resin of Ambrelite ®IRA-45 (manufactured by Organo Co., ltd.) was added to the mixture to neutralize. After the resin was removed by filtration, the filtrate was concentrated to dryness to obtain 45 mg [SIMS m/z 1130 (M+H)] of a crude, powdery, methylated product of guanidylfungin B.

In 3 ml of methanol was dissolved 45 mg of the methylated product. To the solution was added 3 ml of a 1N potassium hydroxide solution. The mixture was stirred at room temperature for 3 hours. Then, the system was neutralized with a 1N hydrochloric acid aqueous solution and the reaction mixture was concentrated to dryness under reduced pressure. The residue was extracted with 20 ml of methanol. After the extract was concentrated to dryness, the residue was dissolved in a small amount of methanol. The solution was applied to a silica gel column (No. 7734, manufactured by E. Merck) which had been prepared by previously saturating it with chloroform. After washing the column with chloroform it was eluted with a solvent mixture of chloroform-methanol-water (65:25:4). The eluted active fraction was concentrated to dryness to obtain 25 mg of the hydrochloride of Compound 3.

EXAMPLE 4

Preparation of Compound 4

In 5 ml of methanol was suspended 50 mg of guanidylfungin B. To the suspension was added 1 ml of a solution of sodium boronhydride in methanol (30 mg/ml). After stirring at room temperature overnight, the system was neutralized with a 1N HCl aqueous solution. The reaction mixture was concentrated to dryness under reduced pressure and the residue was extracted with 10 ml of methanol. The extract was concentrated to dryness, and the residue was reduced guanidylfungin B [SIMS m/z 1118 (M+H)].

After this residue was dissolved in 5 ml of methanol, 5 ml of a 2N potassium hydroxide aqueous solution was added to the resulting solution. The mixture was stirred at room temperature for 3 hours. Then, the system was neutralized with a 1N hydrochloric acid aqueous solution and the reaction mixture was concentrated to dryness under reduced pressure. The residue was extracted with 20 ml of methanol. After the extract was concentrated to dryness, the residue was dissolved in a small amount of methanol. The solution was applied to a silica gel column (No. 7734, manufactured by E. Merck) which had been prepared by previously saturating it with chloroform. After washing the column with chloroform, it was eluted with a mixture of chloroform-methanol-water (65:25:4). The eluted active fraction was concentrated to dryness to obtain 28 mg of the hydrochloride of Compound 4.

EXAMPLE 5

Preparation of Compound 5

Azalomycin $F_4$, 85 mg, was methylated with hydrochloric acid-methanol in a manner similar to Example 3. Then the methylated product was hydrolyzed with potassium hydroxide. The product was purified by silica gel column chromatography to obtain 63 mg of the hydrochloride of Compound 5.

The intermediate, a methylated product of azalomycin $F_4$, was checked by SIMS [m/z 1110 (M+H)].

EXAMPLE 6

Preparation of Compound 6

In a manner similar to Example 4, 120 mg of azalomycin $F_4$ was reduced with sodium borohydride and hydrolyzed with potassium hydroxide. The product was purified by silica gelcolumn chromatography to obtain 90 mg of Compound 6.

The intermediate, a reduced product of azalomycin $F_4$, was checked by SIMS [m/z 1084 (M+H)].

EXAMPLE 7

Preparation of Compound 7

In a manner similar to Example 3, 45 mg of azalomycin $F_3$ was methylated with hydrochloric acid-methanol and hydrolyzed with potassium hydroxide. The product was purified by silica-gel column chromatography to obtain 28 mg of the desired Compound 7.

The intermediate, a methylated product of azalomycin $F_3$, was checked by SIMS [m/z 1096 (M+H)].

EXAMPLE 8

Preparation of compound 8

In a manner similar to Example 4, 40 mg of azalomycin $F_3$ was reduced with sodium borohydride and hydrolyzed with potassium hydroxide. The product was purified by silica gel column chromatography to obtain 25 mg of Compound 8.

The intermediate, a reduced product of azalomycin $F_3$ was checked by SIMS [m/z 1070 (M+H)].

EXAMPLE 9

Preparation of Compound 9

In a manner similar to Example 3, 40 mg of azalomycin $F_5$ was methylated with hydrochloric acid-methanol and hydrolyzed with potassium hydroxide. The product was purified by silica gel column chromatography to obtain 18 mg of Compound 9.

The intermediate, a methylated product of azalomycin $F_5$, was checked by SIMS [m/z 1124 (M+H)].

EXAMPLE 10

Preparation of Compound 10

In a manner similar to Example 4, 30 mg of azalomycin $F_5$ was reduced with sodium borohydride and hydrolyzed with potassium hydroxide. The product was purified by silica gel column chromatography to obtain 21 mg of the desired Compound 10.

The intermediate, a reduced product of azalomycin $F_5$, was checked by SIMS [m/z 1098 (M+H)].

EXAMPLE 11

Preparation of Compound 11

In a manner similar to Example 3, 280 mg of copiamycin was methylated with hydrochloric acid-methanol and hydrolyzed with potassium hydroxide. The product was purified by silica gel column chromatography to obtain 195 mg of Compound 11.

The intermediate, a methylated product of copiamycin, was checked by SIMS [m/z 1072 (M+H)].

EXAMPLE 12

Preparation of Compound 12

In a manner similar to Example 4, 250 mg of copiamycin was reduced with sodium borohydride and hydrolyzed with potassium hydroxide. The product was purified by silica gel column chromatography to obtain 1640 mg of Compound 12.

The intermediate, a reduced product of copiamycin, was checked by SIMS [m/z 1060 (M+H)].

EXAMPLE 13

Preparation of Compound 13

In a manner similcar to Example 3, 30 mg of neocopiamycin A was methylated with hydrochloric acid-methanol and hydrolyzed with potassium hydroxide. The product was purified by silica gel column chromatography to obtain 21 mg of Compound 13. The intermediate, a methylated product of neocopiamycin A, was checked by SIMS [m/z 1058 (M+H)].

EXAMPLE 14

Preparation of Compound 14

In a manner similar to Example 4, 25 mg of neocopiamycin A was reduced with sodium borohydride and hydrolyzed with potassium hydroxide. The product was purified by silica gel column chromatography to obtain 17 mg of Compound 14.

The intermediate, a reduced product of neocopiamycin A, was checked by SIMS [m/z 1046 (M+H)].

EXAMPLE 15

Preparation of Compound 15

In a manner similar to Example 3, 250 mg of scopafungin was methylated with hyrochloric acid-methanol and hydrolyzed with potassium hydroxide. The product was purified by silica gel column chromatography to obtain 122 mg of Compound 15.

The intermediate, a methylated product of scopafungin, was checked by SIMS [m/z 1156 (M+H)].

EXAMPLE 16

Preparation of Compound 16

In a manner similar to Example 4, 250 mg of scopafungin was reduced with sodium borohydride and hydrolyzed with potassium hydroxide. The product was purified by silica gel column chromatography to obtain 144 mg of Compound 16.

The intermediate, a reduced product of scopafungin, was checked by SIMS [m/z 1144 (M+H)].

Effect of the Invention

As described above, demalonylderivatives of the guanidylfungins that are useful as antimicrobial agents, particularly as antifungal agents, and processes for preparing these derivatives are provided by the present invention.

Enhanced antimicrobial activity was noted with the demalonyl derivatives of the guanidylfungins of the present invention as compared to the parent compounds. In addition, the antimicrobial activity is fungicidal and these derivatives are useful as antimicrobial agents. Further, the parent compounds are insoluble in water, whereas the compounds of the present invention provide increased solubility in water and alcohols, and possess a solubility sufficient to utilize them as antimicrobial agents. Furthermore, the compounds of the present invention exhibit a synergestic antifungal effect when used with the imidazole antifungal agents.

What we claim is:

1. A process for preparing a compound represented by general formula (Ia) described below:

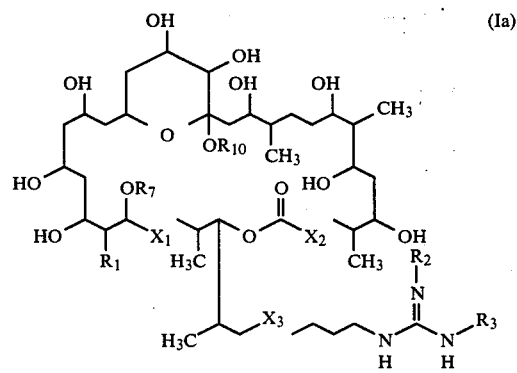

(Ia)

wherein
$X_1$ represents

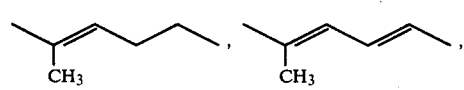

-continued

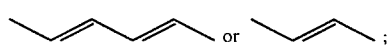

$X_2$ represents

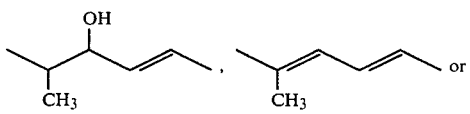

$X_3$ represents

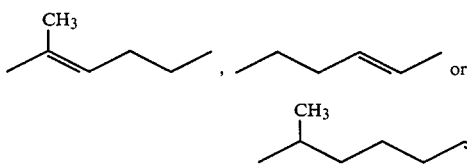

$R_1$ represents H or $CH_3$;
$R_2$ and $R_3$ which may be the same or different, each represent H or a lower alkyl group;
$R_7$ represents H or a lower alkyl group; and
$R_{10}$ represents a lower alkyl group; or an acid salt thereof, which process comprises reacting a compound represented by general formula (II) described below:

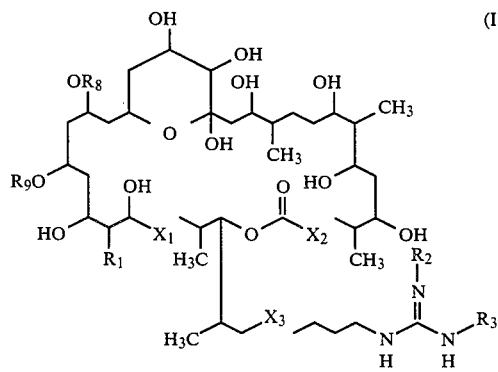

wherein $X_1$, $X_2$, $X_3$, $R_1$, $R_2$ and $R_3$ are as described above and $R_8$ and $R_9$, which are different from each other, each represent H or $COCH_2COOH$, with an alcohol represented by general formula (III) described below:

$$R_{10}-OH \quad (III)$$

wherein $R_{10}$ is the same as described above, in the presence of an acid catalyst to alkylate the compound of general formula (II), and then hydrolyzing the malonic acid monoester.

2. A process for preparing a compound represented by general formula (Ib) described below:

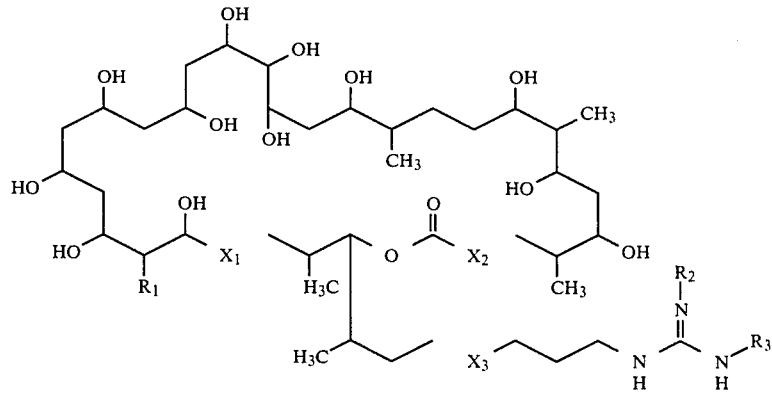

wherein
$X_1$ represents

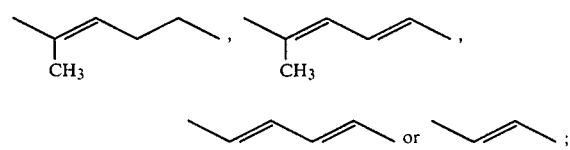

$X_2$ represents

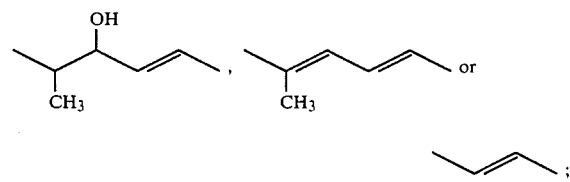

$X_3$ represents

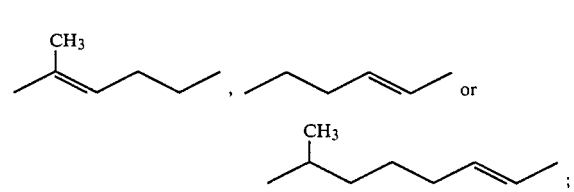

$R_1$ represents H or $CH_3$ and;
$R_2$ and $R_3$, which may be the same or different, each represent H or a lower alkyl group;
or an acid salt thereof, which process comprises reacting a compound represented by general formula (II) described below:

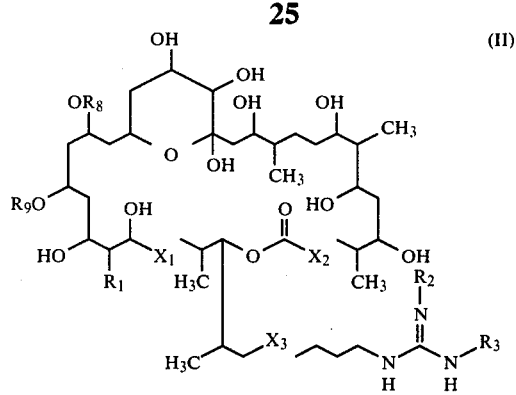
(II)
wherein
X₁, X₂, X₃, R₁, R₂ and R₃ are as described above; and
R₈ and R₉, which are different from each other, each represent H or COCH₂COOH;
with a reducing agent to reduce the hemiketal group, and then hydrolyzing the malonic acid monoester.
* * * * *